US011626198B2

(12) United States Patent
Nolan et al.

(10) Patent No.: US 11,626,198 B2
(45) Date of Patent: Apr. 11, 2023

(54) PATIENT FEEDBACK FOR USES OF THERAPEUTIC DEVICE

(71) Applicant: KONINKLIJKE PHILIPS N.V., Eindhoven (NL)

(72) Inventors: Julian Charles Nolan, Pully (CH); Matthew John Lawrenson, Bussigny-pres-de-lausanne (CH)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 809 days.

(21) Appl. No.: 15/031,291

(22) PCT Filed: Oct. 21, 2014

(86) PCT No.: PCT/EP2014/072473
§ 371 (c)(1),
(2) Date: Apr. 22, 2016

(87) PCT Pub. No.: WO2015/062897
PCT Pub. Date: May 7, 2015

(65) Prior Publication Data
US 2016/0275259 A1 Sep. 22, 2016

(30) Foreign Application Priority Data
Nov. 1, 2013 (EP) ................................. 13191295

(51) Int. Cl.
*G16H 20/30* (2018.01)
*G16H 10/60* (2018.01)
(Continued)

(52) U.S. Cl.
CPC ............. *G16H 20/30* (2018.01); *G16H 10/60* (2018.01); *G16H 40/63* (2018.01); *G16H 40/67* (2018.01)

(58) Field of Classification Search
CPC ..... G06F 19/3418; G06F 19/00; G16H 10/60; G16H 40/63
See application file for complete search history.

(56) References Cited

U.S. PATENT DOCUMENTS 6,272,378 B1 * 8/2001 Baumgart-Schmitt ...................... A61B 5/0476 600/544
2005/0026205 A1 2/2005 Puppe et al.
(Continued)

FOREIGN PATENT DOCUMENTS

| EP | 2549397 A1 | 1/2013 |
| WO | 2010107928 A2 | 9/2010 |
| WO | 2012127337 A2 | 9/2012 |

*Primary Examiner* — Jason S Tiedeman
*Assistant Examiner* — Mohmad Muqueeth

(57) ABSTRACT

The present invention relates to a patient feedback system (10) for providing feedback information on the use of a therapeutic device (14) to a patient (12), said system (10) comprising: an interface (34) for receiving personal profile data (18) of the patient (12); a database (16) for storing reference profile data (18') and reference device settings (54) from a plurality of reference patients (42) using therapeutic devices; a cohort selection module (36) for comparing the personal profile data (18) of the patient (12) with the reference profile data (18') of the reference patients (42) in the database (16) and for determining a cohort (44) for the patient (12) from the plurality of reference patients (42) based upon said comparison, wherein said cohort (44) comprises a subset of the reference patients (42) having reference profile data (18') similar to the personal profile data (18) of the patient (12); and a feedback unit (38) for determining feedback information based on the reference device settings (54) of the reference patients (42) in the cohort (44) and for providing said feedback information to the patient (12).

17 Claims, 3 Drawing Sheets

(51) Int. Cl.
*G16H 40/63* (2018.01)
*G16H 40/67* (2018.01)

(56) References Cited

U.S. PATENT DOCUMENTS

| | | | |
|---|---|---|---|
| 2006/0026205 A1* | 2/2006 | Butterfield | G16H 40/63 |
| 2008/0162182 A1 | 7/2008 | Cazares et al. | |
| 2008/0300914 A1* | 12/2008 | Karkanias | G16H 20/30 |
| | | | 705/2 |
| 2009/0043613 A1 | 2/2009 | Jung et al. | |
| 2009/0055223 A1 | 2/2009 | Jung et al. | |
| 2009/0112114 A1 | 4/2009 | Ayyagari et al. | |
| 2009/0287503 A1* | 11/2009 | Angell | G16H 10/20 |
| | | | 705/3 |
| 2010/0262045 A1 | 10/2010 | Heaton et al. | |
| 2010/0300445 A1* | 12/2010 | Chatburn | A61M 16/0063 |
| | | | 128/204.23 |
| 2011/0015494 A1 | 1/2011 | Dothie et al. | |
| 2012/0053422 A1 | 3/2012 | Rantala | |
| 2012/0116182 A1 | 5/2012 | Brynelsen et al. | |
| 2012/0129139 A1 | 5/2012 | Partovi | |

\* cited by examiner

PATIENT FEEDBACK FOR USES OF THERAPEUTIC DEVICE

CROSS-REFERENCE TO PRIOR APPLICATIONS

This application is the U.S. National Phase application under 35 U.S.C. §371 of International Application Serial No. PCT/EP2014/072473, filed on Oct. 21, 2014, which claims the benefit of European Application Serial No. EP13191295.8, filed on Nov. 1, 2013. These applications are hereby incorporated by reference herein.

FIELD OF THE INVENTION

The present invention relates to a patient feedback system for providing feedback information to a patient and a corresponding method as well as to a therapeutic device.

BACKGROUND OF THE INVENTION

Users of therapeutic devices are often not familiar with the technical and physiological terminology, the operating mode of the device and the required device settings. Thus, the users, i.e. the patients, may feel uncomfortable when using a therapeutic device and may be anxious as to whether this discomfort is an expected side-product of the treatment or whether the treatment has been incorrectly set. If the therapeutic device settings are not chosen appropriately for the patient's situation, this may be causing discomfort that could be avoided.

For instance, in the treatment of diseases such as obstructive sleep apnea syndrome (OSA), patients usually use pressure-support systems or medical ventilators for delivering gas such as air, cleaned air, oxygen or any modification thereof in a pressurized or unpressurized way. OSA is usually caused by an obstruction or partial obstruction of the upper airway. It is characterized by repetitive pauses in breathing during sleep and it is usually associated with a reduction in blood oxygen saturation. Such pauses in breathing, called apneas, typically last 20 to 40 seconds. Less severe but also often causing a decreased amount of air movement into the lungs and a drop in oxygen level in the blood are episodes of overly shallow breathing or an abnormally low respiratory rate, called hypopnea. The obstruction of the upper airway is usually caused by reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied by snoring.

Different invasive and non-invasive treatments for OSA are known. One of the most powerful non-invasive treatments is the usage of continuous positive airway pressure (CPAP) or bilevel positive airway pressure (BiPAP) in which the patient uses a machine (CPAP machine or BiPAP machine) that blows pressurized gas, preferably air, through the airway of the patient in order to keep it open. For this, the patient usually has to appropriately choose settings for this machine (e.g. the air pressure, flow rate or the gas composition) himself. The usual application of such a machine lasts for a longer time and may be uncomfortable for the patient who needs to wear a facial mask and who might not be used to the feeling of having pressurized air be blown into his airways. Then, the patient might be insecure of whether his discomfort is due to the treatment itself or whether this discomfort is due to wrong or suboptimal settings of the therapeutic device.

Other examples for therapeutic devices of which a user himself has to choose at least part of the device settings may be found in the treatment of chronic diseases such as diabetes or others. Also in these application areas, the user is often insecure of how to choose appropriate settings for his device.

WO 2012/127337 A2 proposes methods and systems to promote targeted inter-patient interactions to increase patient adherence. In particular, there are outlined inter-patient networks, such as virtual environments like an online forum which may foster a sense of community among patients and help to promote the patient adherence to a therapy regimen despite practical limitations. In order to overcome such limitations, a virtual environment is proposed in which users are matched (anonymously) in pairs or groups based on usage information of their respective therapeutic devices. A person participating in such a virtual environment may get in contact with other patients using their therapeutic devices in a similar fashion.

US 2009/0043613 A1 discloses a system and method for generating output data based on patient monitoring. One exemplary embodiment includes posting real-time monitoring data regarding the administration of a health-related procedure to a recipient patient to a patient data record. These monitoring data are processed to determine compliance or non-compliance based on a comparison of the health-related procedure with a predetermined benchmark standard. Thus, patient data are collected and formatted to match a predefined standard in order to allow a comparison of a health-related procedure administered to the patient with a predetermined benchmark standard. One focus of the disclosure is to allow a comparison of monitoring data of different patients.

EP 2 549 397 A1 refers to a computer-implemented method for customizing a hearing aid. The method comprising: receiving trial period information comprising one or more of a performance parameter indicative of a performance of the hearing aid during a trial period, a usage parameter indicative of a usage pattern of the hearing aid during a trial period, user profile information indicative of one or more user characteristics, hearing aid information indicative of one or more hearing aid characteristics, and a user feedback parameter indicative of user information about a performance of the hearing aid during the trial period; determining one or more parameter settings of the one or more adjustable parameters based on the received trial period information; wherein determining comprises determining the one or more parameter settings based on the received trial period information, on previous trial period information from a plurality of previous trial periods performed for a corresponding plurality of other hearing aids and users, and on corresponding resulting parameter settings of respective adjustable parameters previously selected for said plurality of other hearing aids.

US 2008/0300914 A1 discloses a system that facilitates management of physical activity by dynamically compensating for current conditions. A user profile can be employed to automatically calibrate an activity device (e.g., treadmill, cycle, haptic brace) based upon characteristics and/or limitations of a user.

However, most patients using therapeutic devices still mostly require the feedback of a physician on how to choose appropriate therapeutic device settings.

SUMMARY OF THE INVENTION

It is therefore an object of the present invention to provide a patient feedback system and method for providing feedback information to a patient. In contrast to previous approaches it is the object of the present invention to provide feedback to the patient and not only or necessarily to connect the patient to other patients. The feedback can relate to e.g. reassurance of the patient regarding his treatment and/or motivating the patient to comply with his treatment. Thereby patient comfort and safety are to be increased. It is further an object of the present invention to provide a therapeutic device comprising a communication interface.

In a first aspect of the present invention, there is provided a patient feedback system for providing feedback information on the use of a therapeutic device to a patient, said system comprising:

a data interface for receiving personal profile data of the patient, a database for storing reference profile data and reference device settings from a plurality of reference patients using therapeutic devices, wherein the reference device settings include at least one device parameter being indicative of how a therapeutic device of a reference patient is configured, a cohort selection module for comparing the personal profile data of the patient with the reference profile data of the reference patients in the database and for determining a cohort for the patient from the plurality of reference patients based upon said comparison, wherein said cohort comprises a subset of the reference patients having reference profile data similar to the personal profile data of the patient and using similar or the same therapeutic devices as the patient, wherein determining the cohort further includes determining for the at least one device parameter a statistical sample size representing a minimum number of reference patients in the cohort required to allow determining statistically relevant feedback information, and a feedback unit for determining feedback information based on the reference device settings of the cohort and for providing said feedback information to the patient.

According to another aspect of the present invention there is presented a patient feedback method for providing feedback information on the use of a therapeutic device to a patient, said method comprises:

receiving personal profile data of the patient, storing reference profile data and reference device settings from a plurality of reference patients using therapeutic devices, wherein the reference device settings include at least one device parameter being indicative of how a therapeutic device of a reference patient is configured, comparing the personal profile data of the patient with the reference profile data of the reference patients in the database, determining a cohort for the patient from the plurality of reference patients based upon said comparison, wherein said cohort comprises a subset of the reference patients having reference profile data similar to the personal profile data of the patient and using similar or the same therapeutic devices as the patient, wherein determining the cohort further includes determining for the at least one device parameter a statistical sample size representing a minimum number of reference patients in the cohort required to allow determining statistically relevant feedback information, and determining feedback information based on the reference device settings of the reference patients in the cohort and providing said feedback information to the patient.

In yet further aspects of the present invention, there are provided a computer program which comprises program code means for causing a computer to perform the steps of the method disclosed herein when said computer program is carried out on a computer as well as a non-transitory computer-readable recording medium having said computer program stored thereon.

Preferred embodiments of the invention are defined in the dependent claims. It shall be understood that the claimed therapeutic device and the claimed patient feedback method have similar and/or identical preferred embodiments as the claimed patient feedback system and as defined in the dependent claims.

A therapeutic device may particularly refer to any kind of apparatus or system being used in a medical treatment of respiratory conditions such as obstructive sleep apnea. Examples include but are not limited to pressurized air generators or medical ventilators such as PAP, CPAP or BiPAP machines. However, aspects, concepts or ideas of the present invention may also be used for other therapeutic devices, such as e.g. drug administration devices, devices for providing movement therapy or other devices actively interfering with a patient in order to provide a therapy of a medical condition (e.g. OSA) of the patient.

Feedback information may particularly refer to information relating to the use of a therapeutic device, such as how the operating parameters of a device are to be chosen or how other patients using a comparable device usually choose their operating parameters. However, the feedback may additionally or alternatively relate to e.g. reassurance of the patient regarding his treatment, motivating the patient to comply with his treatment and/or suggesting ways to improve treatment results. The feedback may be based on the way how other patients (e.g. patients similar to the patient who is given feedback) use their devices (which may be comparable to the device used by the patient who is given feedback) and/or the results they obtain with their therapies.

The personal profile data of a patient are compared to the reference profile data of reference patients. Herein, the distinction between personal profile data and reference profile data has been introduced in order to allow a better description of the functionality of the system according to the present invention. However, both personal profile data and reference profile data basically indicate the same kind of data for different persons or patients. Reference profile data may also be referred to as personal profile data of reference patients. Usually, the parameters included in the personal profile data (profile parameters) have corresponding parameters, i.e. measures of the same property for a different person, in the reference profile data. The same holds for therapeutic device settings and reference device settings. Both refer to corresponding information for the therapeutic device of a patient and the therapeutic device of a reference patient, respectively. Reference device settings may also be referred to as therapeutic device settings of reference patients or as therapeutic device settings of therapeutic devices used by reference patients. Therapeutic device settings of a patient may also be referred to as therapeutic device settings of a therapeutic device used by a patient. Usually, a parameter included in the therapeutic device settings is indicative of one specific setting of a therapeutic device, e.g. a device parameter or operating parameter being indicative of how the device is configured such as the selected flow rate, air pressure or operating hours in case of a PAP machine. Further, a therapeutic device parameter will usually have a corresponding parameter in the reference device settings.

One advantage of the present invention is that a patient is provided with dedicated feedback information on his use of a therapeutic device wherein the feedback information is adapted to his current situation. In contrast to previous approaches, this feedback information is determined based on reference device settings of patients with a comparable background (i.e. the cohort of the patient). The system initially obtains personal profile data of the patient through an interface such as a network or internet connection.

The obtained personal profile data may, for example, relate to any kind of information being indicative of the patient's situation, physiology, or medical situation. Both reference profile data and reference device settings from a plurality of reference patients using therapeutic devices are stored in a database. From these reference patients, there is selected a cohort for the patient, i.e. a peer group of patients with reference profile data comparable to the patient's personal profile data. Therefore, the reference patients can, e.g., be ordered based on how similar their profile data is to the patient's personal profile data. The reference patients with the most similar reference profile data can be selected first.

Then, the reference device settings of the cohort, i.e. the settings of the therapeutic devices of the selected patients with similar personal profile data, are determined. Based thereupon, feedback information as described above is determined and provided to the patient. It is either possible to select a cohort for a patient or to select a cohort for a single therapeutic device setting. It may, in certain cases, be advantageous to select a different cohort for a different device parameter (e.g. select another cohort when evaluating the flow rate of a PAP machine than when selecting the provided air pressure because other profile parameters are relevant with respect thereto).

One possibility to fill the database with relevant reference device settings may consist in directly obtaining reference device settings from therapeutic devices. Such a therapeutic device comprising a communication module may thus directly communicate the relevant information to a patient feedback system. This relevant information, i.e. therapeutic device settings of reference patients, may then be included into the database and used as reference device settings. One advantage thereof is that the contribution of reference device settings can be assured reliably and efficiently.

The provision of the feedback information to the patient may, for example, be realized via a display or screen (e.g. comprised in the feedback unit). It is also possible that the feedback information is provided by making it remotely accessible (e.g. in the internet or in a network), in case the patient feedback system is network-based. Usually the feedback information is prepared in a meaningful way, for example by means of a graphical representation in form of a diagram visualizing the chosen reference device settings of reference patients in the cohort. Such a graphical representation may, for example, be a percentage-evaluation of the number of reference patients that choose a specific setting, a percentile distribution or the like.

The patient thus obtains dedicated feedback on how other patients with comparable profiles (comparison of personal profile data of the patient to reference profile data, i.e. personal profile data of the reference patients) use their therapeutic devices. The feedback information may particularly include parameters being indicative of the mean, the standard deviation, the quantiles or other statistical evaluations being determined based on the reference device settings of the patients in the cohort (which therapeutic device settings they choose). For instance, there may be provided the mean value of the flow rate selected by the reference patients in the cohort. On the one hand the system provides a way for a patient to gain feedback that his/her use of a therapeutic device (e.g. PAP machine) is within the usual 'norms' given his/her personal profile data (e.g. data including information on his/her physique, level of apnea etc.). On the other hand the system may also provide a basis for a patient to form questions to discuss with a medical practitioner (physician or other medical personnel).

A further advantage of the present invention is that the user, i.e. the patient, is given feedback on how he is using his therapeutic device without needing to interpret whether another patient's use of a therapeutic device, i.e. another patient's therapeutic device settings, are at all relevant for his own situation. The system automatically and autonomously determines/selects a cohort (i.e. a comparison group) and determines feedback information including information on the therapeutic device settings of the cohort. Thus, the patient may obtain dedicated and relevant feedback information without needing to consult a physician or other medical personnel. The system does not (necessarily) require any input of physicians or medical personnel. If, for instance, a patient using a PAP machine requires feedback as to which pressure to choose for the ventilation, the patient feedback system according to the present invention may provide this information. A single patient may compare his therapeutic device settings with reference device settings chosen by reference patients stored in the database.

According to a preferable embodiment of a patient feedback system according to the present invention, the feedback information includes a deviation parameter being indicative of the deviations of the therapeutic device settings of the patient from the reference device settings of the reference patients in the cohort.

The feedback information thus not only includes an evaluation of how the reference patients in the cohorts have chosen their reference device parameter but includes a statistical evaluation (deviation parameter) thereof in particular with regard to the therapeutic device settings that the patient himself has chosen. For instance, the feedback information may include a deviation parameter that indicates that the patient has chosen one of the parameters of his therapeutic device (therapeutic device settings) completely different from all other users in his cohort (i.e. a high deviation). The user may then take this as an indicator that his chosen setting might not be optimal for his current situation. This may be expressed by means of a deviation parameter. Alternatively, if the patient chooses all settings of his therapeutic device in agreement with the corresponding reference device settings from his cohort, the feedback information may merely include an indication (i.e. a binary deviation parameter) that everything is alright.

One advantage of this embodiment is that the patient immediately obtains feedback information on the use of a therapeutic device that is relevant to his specific situation. The feedback information is determined based upon a group of reference patients (cohort) that have comparable personal profile data and for whom it is this likely to be in a comparable medical situation. Yet another advantage of this embodiment of the present invention is that a patient can immediately see which of his settings is in disagreement with his cohort, i.e. has a high deviation. The patient does not require individually inspecting other patients and their use of their therapeutic devices but is provided with a deviation parameter being calculated based on a statistical evaluation and summarizing all relevant information.

According to another embodiment, there is further comprised a therapy module for determining suggested therapeutic device settings based on the reference device settings of the reference patients in the cohort and the feedback information includes the suggested therapeutic devices settings.

In addition to providing an evaluation of the cohort's therapeutic device settings, there may be determined (suggested) appropriate therapeutic device settings. Such suggested therapeutic device settings may particularly refer to settings being used by other patients in a similar situation. Optimally, a patient using a therapeutic device obtains a suggestion which setting to choose for his device. This suggestion can be based on the experience of other users. For instance, if the majority of users have found that a particular setting is appropriate in a certain situation, then the therapy module will return this setting as a suggested therapeutic device setting.

One particular advantage of this embodiment is that the patient is not only provided with information how other people choose their therapeutic device settings, but directly gets a recommendation adapted to his particular situation. This makes the choice of appropriate therapeutic device settings a lot more comfortable. Yet another advantage is that the therapy module may also provide its recommendations (suggested therapeutic device settings) based on an inclusion of the specific situation of the patient (personal profile data).

According to yet another embodiment, there is further comprised a formatting module for converting the personal profile data received via the interface into a standard format.

For comparing personal profile data with reference profile data, the format and/or the nomenclature must be comparable. Thus, in order to format or convert data coming into the system, a formatting module is provided. One advantage of the formatting module as disclosed herein is that data of patients in different situations (different reference profile data) may be used. The personal profile may be converted and brought into a standard format by means of this formatting module. The formatting module may also include lookup table functionality for converting personal profile parameters being indicated on different scales into a single scale (standard format).

According to another embodiment, there is provided a patient feedback system as described above, wherein the personal profile data or the reference profile data, respectively, include at least one profile parameter being indicative of a sleep profile of the patient or a reference patient, respectively, in particular a sleep duration and/or an apneahypopnea index, physiological data of the patient or the reference patient, respectively, in particular the sex, age, weight or height of the patient or the reference patient, respectively, a vital sign of the patient or the reference patient, respectively a medical history of the patient or the reference patient, respectively and a type and/or a serial number of the therapeutic device used by the patient or the reference patient, respectively.

In particular in applications of ventilating devices, e.g. therapeutic devices in the treatment of apnea-related conditions, the personal profile data or reference profiled data may include a profile parameter being indicative of the sleep profile or the sleep architecture of the patient. Such a profile parameter may either be determined by a sleep-monitoring device such as, e.g. a device evaluating the snoring sounds or the movements of a patient during the night, or may also be determined qualitatively by a physician in a sleep laboratory. Of particular interest may be to use the apneahypopnea index (AHI) as profile parameter. In sleep medicine, this index refers to the average number of apnea- and hypopnea episodes per hour of sleep. The apneahypopnea index is often used as an index of the severity of a sleep apnea. Usually only apneas are counted that last for at least ten seconds, and, as a result thereof, may be associated with a decrease in blood oxygenation. Further important for this example are also physiological data of the patient for considering effects resulting, e.g. from overweight, age, gender etc. of a patient. Such effects may influence how a therapeutic device needs to be configured optimally. Other types of physiological data being of particular importance for other medical conditions may also be included.

Further, the profile data (personal or reference profile data), may include a profile parameter being indicative of a vital sign of the patient or the reference patient, respectively. A vital sign may, e.g., be determined by a vital sign monitoring device such as a heart-rate monitoring device, a blood oxygenation saturation monitoring device, a movement sensor or another technical system for automatically obtaining vital sign data of the patient. Alternatively, a vital sign may also be determined based on input from a physician or other medical personnel carrying out dedicated measurement procedures.

Still further, the profile data may include profile parameters being indicative of the medical history of the patient or a reference patient. Corresponding profile parameters may, e.g. represent information on behavioral data such as the typical level of nicotine/alcohol intake, the severity of a medical condition or the like. The information may be represented in actual units or on a (numeric) scale (such as a 1-10 scheme) being defined (qualitatively) by a physician. Different profile parameter formats may be possible therefore.

Still further, a meaningful comparison of the patient's therapeutic device settings to the reference device settings of the reference patients in the cohort is usually only possible if reference patients using comparable reference devices are selected. Including a profile parameter being indicative of type and/or serial number of the therapeutic devices (or the reference devices) allows filtering thereupon. Thus, it becomes possible to include only patients using comparable therapeutic devices into the cohort and the comparison may be more meaningful. If also the therapeutic device's serial number is considered as a profile parameter it may even become possible to evaluate effects resulting from manufacturing tolerances between individual therapeutic devices of the same type.

One advantage of including a variety of different profile parameters being indicative of different phenomena is that it becomes possible to cover a variety of therapeutic devices and medical conditions. If the patients in the cohort are very similar, i.e. have similar profile parameters, the validity and significance of the determined cohort may be increased.

In yet another embodiment the personal profile data further include an importance factor for the at least one profile parameter being indicative of the importance of said at least one profile parameter when determining the cohort and a range value for the at least one profile parameter being indicative of a tolerable offset when determining the cohort.

One advantage of including an importance factor for a parameter (in particular for each of the personal profile parameters) is that it becomes possible to assign different weights to the different profile parameters. These importance factors or weights may be determined by a physician or medical personnel being experienced in how a specific profile parameter may affect the progress of a medical condition. For instance, if it were known that heavy patients (profile data) usually need to select a completely different ventilating pressure (therapeutic device setting) in their lung ventilator (therapeutic device) than light patients it may lead to a more significant cohort if this profile parameter is attributed a higher importance when reference patients are to be selected into the cohort of this patient. By providing an importance factor it becomes possible to include such effects when determining the cohort.

The advantage of providing a range value for a parameter is that it can be indicated within which range of said profile parameter a corresponding profile parameter in the reference profile data should be for selecting the corresponding reference patient into the cohort. For instance, a range value for the profile parameter "age" may be indicative of the age range of the reference patients to select into the cohort. The range value is usually on the same scale as the parameter. If, for example, there is comprised a profile parameter representing the severity of a medical condition, this profile parameter is usually indicated on a scale as determined by a physician. Then the range value is usually on the same scale. The definition of a tolerable offset (an adequate range value for a profile parameter) may, for example, be provided by a physician based on his experience. Including both an importance factor as well as a range value has the advantage that the inclusion of the range of one specific profile parameter when determining a cohort can be in dependence on its importance.

According to yet another embodiment said comparison of the personal profile data of the patient with the reference profile data of the reference patients is based on said range value and said importance factor.

Basing the comparison in the cohort selection module on the range value allows exploiting the above-mentioned advantages. A cohort may be selected based on the different profile parameters and their range values. It may, e.g., be possible to select into the cohort all reference patients that have their corresponding profile parameter within the specified range (range value). The same holds for the importance factor. If, e.g., it is known, that one specific profile parameter is not so important for the medical condition of a patient, this profile parameter may also be considered to be not so important when determining a cohort. It may, e.g., be preferable to include reference patients that are different with respect to a profile parameter that is of lower importance into the cohort as the cohort will still allow obtaining meaningful feedback information for the patient. This is especially important as a cohort usually needs to include a sufficient number of reference patients in order to allow for a meaningful comparison of the therapeutic device setting with the reference device settings.

According to another embodiment, the reference device settings include at least one device parameter being indicative of how a therapeutic device of a reference patient is configured, and determining the cohort for the patient from the plurality of reference patients includes determining for the at least one device parameter a statistical sample size representing a minimum number of reference patients in the cohort required to allow determining statistically relevant feedback information.

It is important that the number of reference patients in a cohort is sufficiently high in order to provide a statistically relevant cohort size. For determining an appropriate size of the cohort, it is possible to calculate the desired size based on statistical considerations (a statistical sample size). For instance, a desired power of a statistical test can be defined and the sample size (number of patients in the cohort) can be chosen based on the expected or desired standard deviation. The minimum number of patients in a cohort may also be referred to as minimum statistically relevant cohort (MSRC). The cohort size is then usually chosen to be at least equivalent to this MSRC. Selecting patients into a cohort may start with the reference patients who are the closest or most similar (i.e. who have the most similar profile parameters) to the patient. Then, in order to include a sufficient number (e.g. at least the MSRC) of reference patients other reference patients can be added whose reference profile data are increasingly different until the MSRC is reached. The selected cohort is usually chosen to represent the group of users (reference patients) most similar to the patient. The advantage of defining the MSRC as outlined above is that the cohort size is sufficient for allowing a statistically relevant evaluation of the reference device settings of the reference patients in the cohort but that the cohort nevertheless mainly includes meaningful reference patients, i.e. reference patients that are similar with regard to their reference profile data. On the one hand the cohort has to include a sufficient number of reference patients. On the other hand, the cohort should be limited to comparable patients, i.e. reference patients with comparable profile data. For this it is usually helpful to rely on statistical considerations when defining the MSRC.

According to another embodiment the personal profile data further include a range value for the at least one profile parameter being indicative of a tolerable offset when determining the cohort, said comparison of the personal profile data of the patient with the reference profile data of the reference patients is based on said range value for the at least one profile parameter and determining the cohort for the patient from the plurality of reference patients further includes adjusting said range value until a number of reference patients in the cohort is substantially equal to said statistical sample size.

Thus, the comparison for each personal profile parameter is not only based on the initially specified range value, but the range value is adjusted dynamically. By changing the range value, it becomes possible to dynamically adjust the size of the determined cohort. If, e.g., the initial cohort is too small, the range value is increased and more reference patients lie within the range with their corresponding profile parameters. As outlined above, the range value is increased until the statistical sample size is reached. If the determined statistical sample size is no a rational number, substantially equal usually means that the next higher (or alternatively lower) natural number of patients is selected. By increasing the range value it is assured that those patients are included into the cohort that are the most similar, i.e. that have as similar as possible profile parameter parameters to the corresponding profile parameters in the reference patients reference profile data. The advantage of dynamically adjusting the range value is that the number of reference patients in the cohort is as big as necessary but as small as possible. Thus, the determined feedback information may be accurate enough (because it is based on a sufficiently big cohort) but is still statistically relevant and allows the determination of meaningful feedback information.

According to another embodiment, receiving personal profile data of the patient includes receiving personal profile data from a monitoring device measuring the at least one profile parameter being indicative of the sleep profile and/or the vital sign of the patient.

If a monitoring device may directly contribute collected monitoring data to the patient feedback system as personal profile data for the patient being monitored, the personal profile data of the patient may be collected efficiently. Such a monitoring device may particularly refer to a sleep monitoring device, which automatically determines parameters (profile parameters) related to the sleep of a patient. Such profile parameters may include the duration of the sleep or the apnea-hypopnea index of a patient determined by means of evaluating noise (e.g. snoring noise) or movements originating from the patient. Further, a monitoring device may also refer to a vital sign monitoring device, such as a heart-rate monitoring device making use of sensors (cameras, microphones, blood pressure, etc.) or making use of a body area sensor network. The monitoring device can be part of the patient feedback system and directly or remotely connected thereto for providing the measured data. The advantage thereof is that the patient has to contribute fewer of his personal profile data manually. Also, the reliability of the personal profile data may be increased.

According to another embodiment, the interface is further suitable for receiving personal profile data and/or therapeutic device settings from patients willing to contribute reference profile data or reference device settings to the database.

One advantage of this embodiment is that it becomes possible to automatically fill the database with data (profile data and device settings) from reference patients. Each patient may directly contribute his personal profile data to the database. These data may also be converted to an appropriate format by means of a formatting module as described above. Personal profile data are then stored in the database as reference profile data. Therapeutic device settings are stored in the database as reference device settings. Then, a patient that has contributed data may obtain feedback information. In this embodiment, the system functions comparable to a social network, where users (patients) contribute data in order to obtain access to other users (patients) data. Thus, every patient is part of the reference patients for the other patients. The advantage thereof is that the database is filled automatically and may grow dynamically. Also the database is usually always up-to-date.

In another embodiment the therapeutic device is configured to provide a flow of pressurized gas to the patient.

The therapeutic device may thus be a medical ventilator, in particular a positive airway pressure (PAP) machine, a continuous positive airway pressure (CPAP) machine or a bilevel positive airway pressure (BiPAP) machine for moving air into the lungs of a patient. Then, the therapeutic device settings may include device parameters such as the selected airflow, pressure or operating hours. In case of a therapeutic device being configured to provide a flow of pressurized gas to the patient it becomes particularly important to provide feedback to a patient using the device. Often, patients using such medical ventilators feel uncomfortable. Especially during their first use this may be due to wrong or inappropriate settings of the desired pressure or flow rate. One result therefrom may be that the compliance of these patients decreases. The present invention helps to overcome this problem by providing feedback information and patient feedback to these patients. Such therapeutic devices may particular be configured to be used in the treatment of obstructive sleep apnea, chronic obstructive pulmonary disease or diabetes-related pulmonary conditions.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
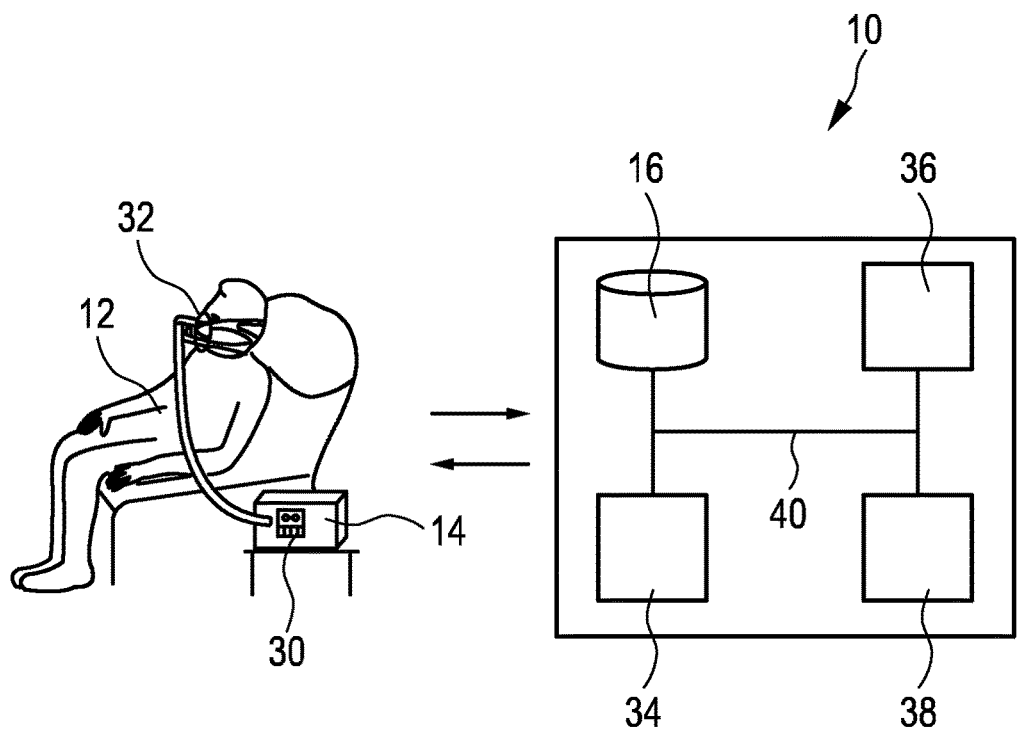
FIG. 1 shows a schematic illustration of a first embodiment of a patient feedback system according to the present invention.

FIG. 1 schematically illustrates a first embodiment of a patient feedback system 10 according to the present invention. Said system 10 may be used for providing feedback information to a patient 12 on the use of a therapeutic device 14. Thereby the system 10 provides a way for a patient 12 to either gain feedback that his/her use of the therapeutic device 14 is within the usual "norms" given the physique, age, type and extent of the disease of the patient 12, or it provides a basis for the patient 12 to change the settings of the therapeutic device 14 if the settings of the therapeutic device 14 are outside the normal use. In order to judge whether the patient 12 uses the therapeutic device 14 in the correct manner, the system 10 compares the personal profile data of the patient 12 with a plurality of personal profile data of other users (herein denoted as reference patients) stored in a database 16. The system 10 then determines the reference patients having similar or identical profile data as the patient 12, e.g. having the same or similar age, the same or similar physics and the same or similar type and extent of disease. Based on statistical analysis of the patient's personal profile data in comparison to the profile data of the reference patients (herein denoted as reference profile data), a cohort is determined in order to find a group of reference patients that are so-to-say similar to the patient 12. The system 10 then provides feedback (feedback information) to the patient 12 how the other users (reference patients) use their therapeutic devices (herein denoted as reference devices). The system 10 may thereto, for example, show the device settings of the reference patients (herein denoted as reference device settings) in the found cohort to the patient 12, such that the patient 12 may compare his/her personal device settings to said reference device settings.

The following terms are used herein: "Personal profile data" denote the profile data of the patient 12. "Reference profile data" denote the profile data of the reference patients, which reference profile data are stored in the database 16. Similarly, "personal device settings" denote the device settings of the patient 12 and "reference device settings" denote the device settings of the reference patients (i.e. the device settings of the devices used by reference patients).

Figure 4:
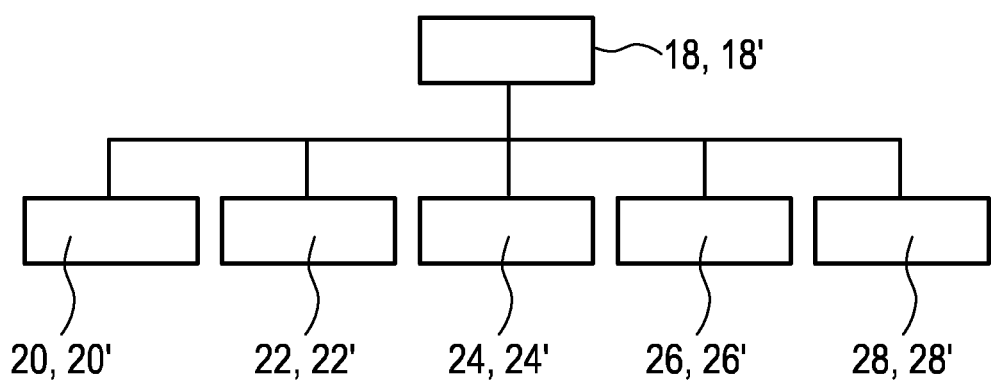
FIG. 4 shows a schematic illustration of possible profile parameters.

As illustrated in FIG. 4, personal profile data 18 or reference profile data 18', respectively, usually include (i.e. are represented by) one or more profile parameters. Such profile parameters may, for example, include at least one parameter 20 being indicative of a sleep profile of the patient 12 or reference patient, respectively. For instance, this sleep profile parameter 20 may correspond to the apnea-hypopnea index, which indicates the number of apneas and hypopneas per sleep time. Further profile parameters 22 could be indicative of physiological data of the patient. Examples for such parameters 22 include the sex, weight, height, neck size or age of the patient 12 or reference patient, respectively. Still further, profile parameters 24 could be indicative of vital signs of the patient 12 or reference patient, respectively. For instance, there may be parameters 24 representing the heart rate, blood oxygen saturation, blood pressure or body temperature. Still further, personal profile data may include profile parameters 26 being indicative of the medical history of the patient 12 or reference patient, respectively, such as the number of cigarettes smoked per day, the amount of alcohol the patient 12 or reference patient regularly consumes or a parameter indicating the severity of a chronic disease. Lastly, profile parameters 28 identifying the therapeutic device 14 of the patient 12 or the reference patient could be included as well in the profile data 18, 18' (in the personal profile data 18 of the patient 12 as well as in the reference profile data 18' of each of the reference patients. Such parameters 28 may include a type identifier, i.e. a device type identifier indicating which type of device 14 the patient 12 or reference patient uses, or a serial number for uniquely identifying the exact device 14 the patient 12 or reference patient uses.

Figure 2:
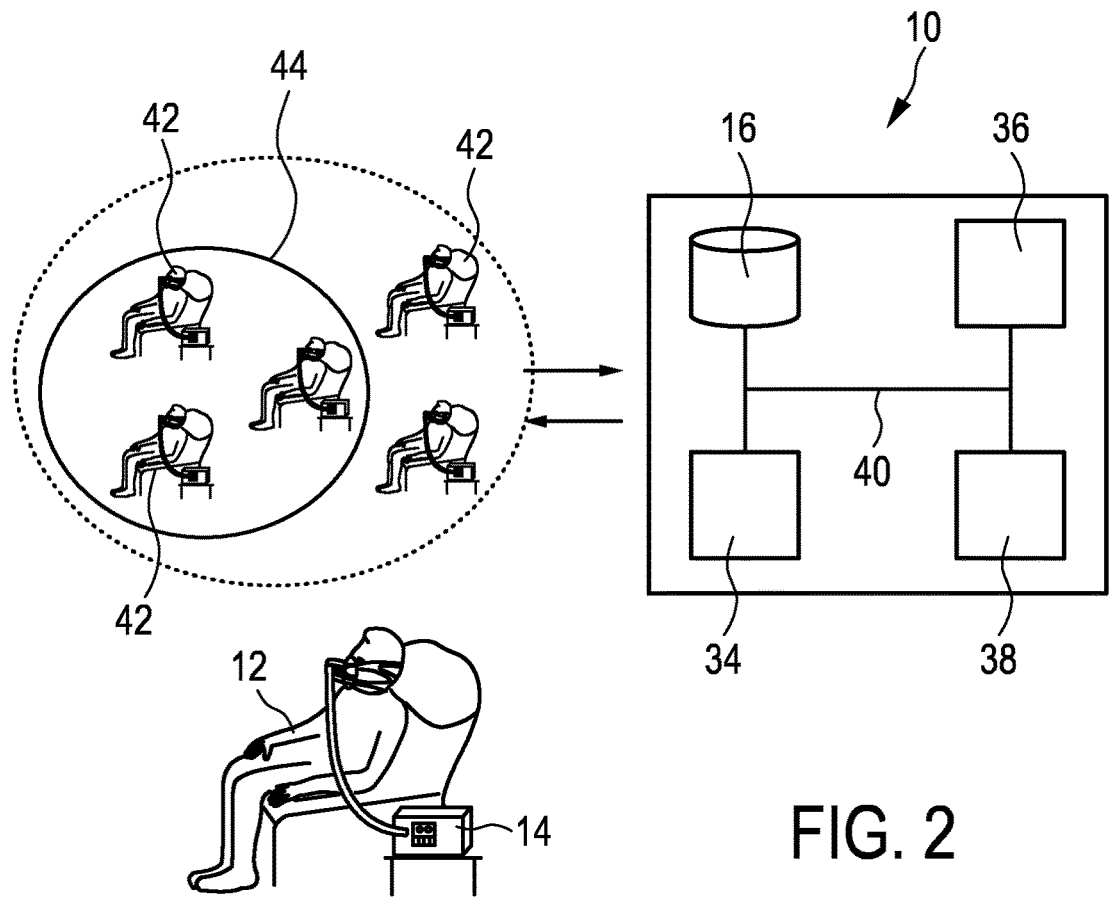
FIG. 2 shows a schematic illustration of another embodiment of the patient feedback system.
Figure 3:
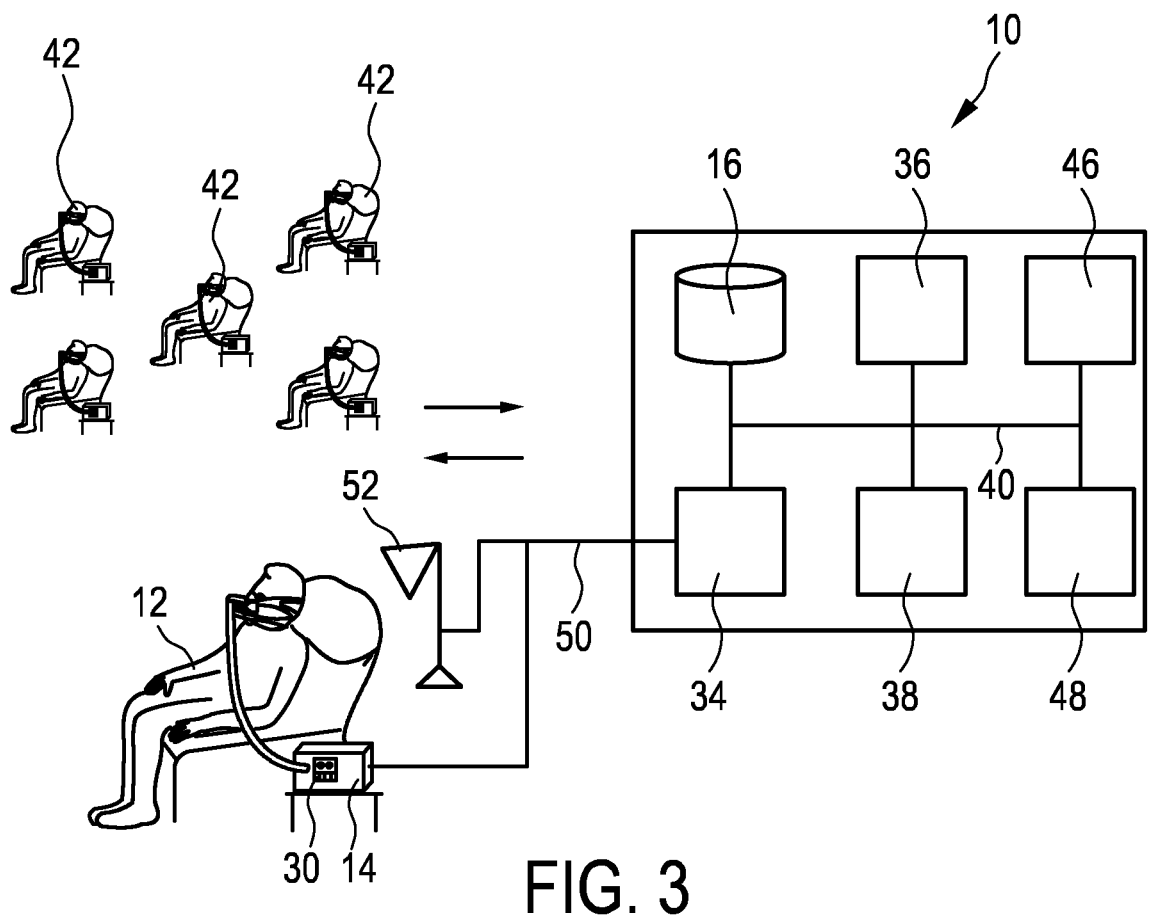
FIG. 3 shows a schematic illustration of yet another embodiment of the patient feedback system.

In FIGS. 1-3, the invention is illustrated on the basis of a medical ventilator device representing the therapeutic device 14. Such a medical ventilator device 14, e.g. a positive airway pressure machine or a continuous positive airway pressure machine, is usually used to provide a flow of pressurized gas to the patient 12. As illustrated in FIG. 1, the therapeutic device 14 provides control elements 30 for choosing different therapeutic device settings. The control elements 30 usually allow selecting therapeutic device parameters being indicative of how the therapeutic device 14 is configured, i.e. how the operating settings of the therapeutic device 14 are set. Such device parameters may be a pressure level, a flow rate or an inhalation gas composition to be provided to the patient 12. The flow of pressurized gas is supplied to the at least one of the patient's respiratory orifices (mouth or nose) via a patient interface 32, i.e. a mask 32. Although the following exemplary embodiments are outlined based on a medical ventilator, the invention is not limited to such medical ventilators, but may also be used for other therapeutic devices.

As illustrated in FIGS. 1-3 the system 10 usually comprises an interface 34 for receiving the above-mentioned personal profile data of the patient 12. It furthermore comprises the database 16 for storing reference profile data and reference device settings. Still further, the system 10 comprise a cohort selection module 36 for comparing the personal profile data of the patient 12 with the reference profile data of the reference patients in the database 16 and for determining a cohort for the patient 12 from the plurality of reference patients based upon said comparison. Finally, the patient feedback system 10 comprises a feedback unit 38 for determining feedback information and for providing said feedback information to the patient 12. There is also illustrated in FIGS. 1-3 that the different elements are usually connected, e.g. by means of a data bus 40 for providing data transfer between the different elements.

According to the first embodiment of the invention illustrated in FIG. 1, the patient 12 is in direct communication with the patient feedback system 10. The interface 34 for receiving the personal profile data 18 may be represented by a human machine interface such as a keyboard of a personal computer directly connected to the system 10. Thus, the patient 12 may use said interface in order to type in his/her age, sex, weight, height and the amount of cigarettes he/she smokes per day (personal profile parameters 20-28). In the system 10, the personal profile data 18 of the patient 12 are then compared to reference profile data in the database 16. In other words, the plurality of personal profile parameters 20-28 are compared to the reference profile parameters 20'-28' of the reference patients that are stored in the database 16.

According to this first embodiment, the reference profile data 18' including the profile parameters 20'-28' of the reference patients may have been entered into the database 16 beforehand and may, for example, originate from a medical study or from a large-scale data collection. Based on the comparison, there is determined a cohort for the patient 12 which cohort includes a subset of the reference patients in the database 16 having similar profile data as the patient 12. The feedback information as determined in the feedback unit 38 may then be provided to the patient 12. For instance, the patient 12 may obtain a list of the device parameters that had been chosen by the reference patients in the patient's 12 cohort.

Further according to the first embodiment illustrated in FIG. 1, the feedback unit 38 may include a display or screen for directly displaying the determined feedback information to the patient 12. Alternatively, the system 10 may also be connected to a display or screen or to a personal computer or laptop or the like. The patient 12 may then use the displayed feedback information in order to control whether the settings he/she used for his/her therapeutic device 14 are correct/normal or if all the other user that were found to be similar to the patient 12 use completely different device settings (reference device settings) for their devices. The patient 12 may then, for example, manually adapt his/her device settings accordingly.

It may also be possible that the system 10 is not spatially located in proximity of the patient 12. Then the interface 34 may be represented by a network or internet connection means such as a wireless or wired network adaptor, a mobile communication module or the like. The patient 12 may then provide his personal profile data by means of an appropriate network-capable device such as a laptop, smartphone, tablet PC that is connected to the system via the interface 34. Similarly, the determined feedback information may then also be provided through the interface 34. For instance, the interface 34 may include a web interface that allows the patient 12 to connect thereto remotely. He may then enter his personal profile data 18 and directly obtain a visualization of the determined feedback information.

In FIG. 2 there is illustrated another preferable embodiment of the patient feedback system 10 according to the present invention. Herein, the system 10 is operated in a social network manner. A plurality of reference patients 42 contributes both their profile data (reference profile data 18') as well as their therapeutic device settings (reference device settings) to the database 16. This contribution may thereby also be effected through an interface including a network or internet connection as described above. Then, the system 10 allows determining a cohort 44 for the patient 12 representing a subset of the reference patients 42.

In short, this means that the difference of the second embodiment shown in FIG. 2 to the first embodiment shown in FIG. 1 is that the database 16 according to the second embodiment is not a preprogrammed database but an interactive database that changes all the time a new reference patient 42 contributes to the database 16 by entering his/her profile data 18' and his/her device settings. If the patient 12 (patient currently under consideration) also provides his/her device settings to the database 16 (via the interface 7), said patient 12 may also be considered a reference patient 42 for any other user of the system 10. However, it is to be noted that the requirement for being a reference patient 42 for others is that the patient 12 also contributes his/her therapeutic device settings. On the other hand, it is not necessary that the patient 12 enters his/her device settings to the database 16 when he/she is only willing to profit from the system 10 while he/she is not willing to contribute to the database 16. In order to receive feedback information and determine the patient's cohort 44, the patient 12 only has to enter his/her personal profile data 18 (but not necessarily his/her personal device settings).

According to a further embodiment of the system 10, the cohorts that had been determined for the reference patients 42 in a similar way as described above for patient 12 may also be stored in the database 16 in connection with each of the reference patients 42 (in a lookup table storing for each reference patient 42 his/her cohort). If the cohort selection module 36 of the system 10 then e.g. finds an almost 100%-match for the patient 12, i.e. a reference patient 42 that has exactly the same or almost exactly the same profile data 18, then the cohort of this particular reference patient 42 may be also taken as the cohort 44 of patient 12. This may help to reduce the computational effort resulting from individually determining a cohort every time a patient requests feedback information. Storing the cohorts for each reference patient 42 may also make it possible to mutually include patients in the respective cohort and thereby optimize the cohort definition/determination.

In the illustrated embodiment in FIG. 2, the system 10 may, for example, be represented by a server device being connected to a network or to the internet for providing the service to patients using therapeutic devices to provide feedback information to them.

In FIG. 3, there is illustrated yet another embodiment of a system 10 according to the present invention. As illustrated therein, the system 10 further comprises a therapy module 46 for determining suggested therapeutic device settings. This therapy module 46 determines suggested therapeutic device settings for the patient 12 based on the reference device settings of the reference patients 42 in the cohort 44 of the patient 12. Thus, the patient 12 does not only receive an evaluation of how the reference patients 42 in the cohort 44 use their reference devices. In addition thereto, the patient 12 receives more or less precise instructions of how to set the operating parameters (device settings) of his/her therapeutic device. For instance, the patient 12 may receive a suggestion of how to set the flow rate of his medical ventilator 14 in order receive an adequate treatment.

Further illustrated in FIG. 3, the system 10 comprises a formatting module 48 for converting personal profile data into a standard format. If, for instance, the patient 12 provides his/her personal data 18 in a non-standard format, the data 18 may need to be converted prior to be compared to the reference profile data 18'. One possible implementation of this formatting module 48 includes lookup table functionality. This lookup table functionality may allow converting parameters indicated in different measurement units into one another or convert between different nomenclatures for the same parameter. For instance, if the patient 12 provides his weight in pounds albeit the reference data 18' in the database 16 are indicated in kilograms, this would require a conversion. Also values of personal profile parameters 20-28 being indicative of a sleep profile, physiological data, vital signs, the medical history of a patient and the type of a used therapeutic device may be grouped and thereby be brought into a standard format. According to further possible embodiments, the formatting module 48 may also allow the conversion of therapeutic device settings (e.g. devices of different types) into a standard format.

As further illustrated in FIG. 3, the therapeutic device 14 of the patient 12 may also be directly connected to the system 10. For this, the therapeutic device 14 may include an appropriately configured communication interface (not shown), e.g., a network or internet connection means. Through this communication interface, the therapeutic device 14 may directly communicate with the system 1 via the interface 34 (as indicated by line 50). On the one hand, this may allow that personal therapeutic device settings of the patient's 12 device 14 are directly communicated to the system 10. Thus, the therapeutic device 14 determines its device parameters (e.g. which flow rate the patient 12 has selected) and automatically communicates them to the system 10 to be included in the database 16. On the other hand, the feedback information including the device settings of the reference patients 42 (reference device settings) in the cohort 44 may be directly fed into the therapeutic device 14 in order to automatically adapt the personal device settings of the patient's 12 therapeutic device 14 according to the reference device settings. In this case the patient 12 does not even have to look up how the other patients (reference patients 42) set their devices, as the therapeutic device 14 does this automatically and adapts thereto.

As further illustrated in FIG. 3, the system 10 may also be connected to a monitoring device 52. Such a monitoring device 52 may comprise a sensor such as a body mounted sensor, a camera, a microphone or the like. The monitoring device 52 may measure a profile parameter, e.g. a vital sign or an apnea related parameter. Such monitoring device 52 may, for example, include a sleep monitoring device recording the snoring sounds or other parameters of the patient 12 suffering from sleep apnea or a body sensor network recording the heart rate or the blood oxygen saturation of the patient 12. If the monitoring device 52 is further directly connected to the patient feedback system 10, it becomes possible to directly communicate the personal profile parameters and include them into the database 16. Thus, at least part of the personal profile parameters 18 can be determined and included in the database 16 automatically. The patient 12 will, however, usually still need to enter other of his/her personal profile parameters (e.g. his age, weight, sex etc.) manually.

Figure 5:
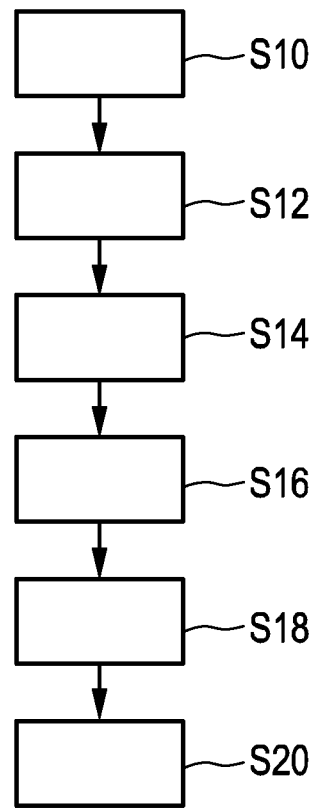
FIG. 5 shows a schematic illustration of an embodiment of a patient feedback method according to the present invention.

FIG. 5 illustrates a patient feedback method according to the present invention. As illustrated, personal profile data of the patient 12 are received in the first step S10 via the data interface 34. Thereby it is as well possible that the patient 12 or his physician enters the data directly into the system 10 by means of a personal computer or keyboard or through a remote connection, e.g. an internet connection. Alternatively, the data may also come from the monitoring device 52 as outlined above. Further, reference profile data 18' and reference device settings from a plurality of reference patients 42 using therapeutic devices are stored in the database 16 in step S12. This storing may also have been carried out prior to receiving the personal profile data 18 of the patient 12 as described above. The method further comprises comparing the personal profile data 18 of the patient 12 with the reference profile data of the reference patients 42 in the database 16 (step S14) and determining the cohort 44 for the patient 12 (step S16). Therefrom, there is then determined feedback information in step S18, which feedback information is then provided to the patient 12 in step S20, e.g. by means of making the data accessible through a network or trough the internet or by displaying the feedback information on a screen.

The above-mentioned method is preferably carried out by the system 10 as outlined above.

Figure 6:
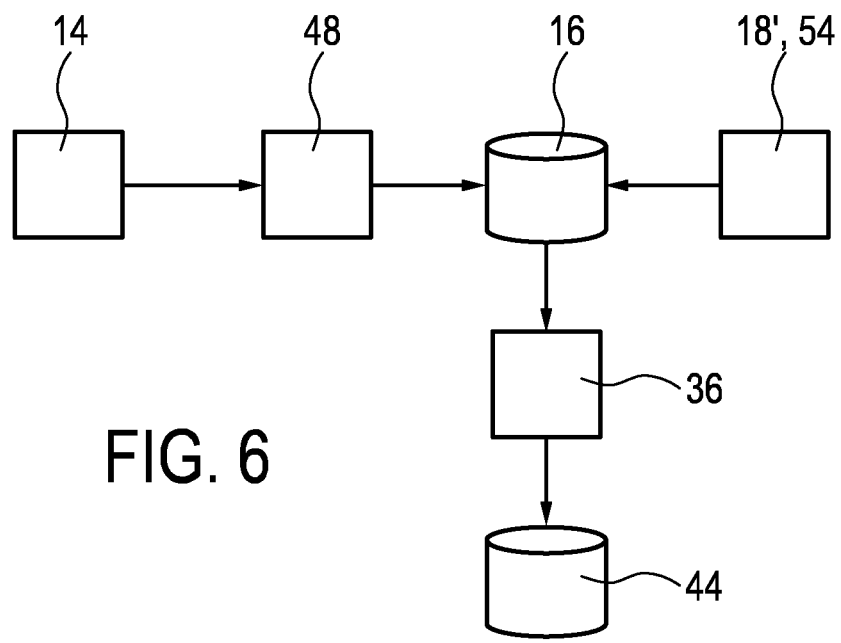
FIG. 6 shows a schematic illustration of the information flow when determining a cohort in the patient feedback system according to the present invention.

In the following, a concrete example of the information flow within the method and system according to the present invention is illustrated in FIG. 6. As illustrated in FIG. 6, the database 16 directly obtains device parameters from the therapeutic device 14. Prior to be stored in the database 16, the device parameters are preprocessed, e.g. by means of the above-mentioned formatting module 48. This preprocessing may include a lookup table comparison for converting names and measurement units (of the therapeutic device settings or the device parameters, respectively) to a standard format. There are further stored in the database 16 reference profile data 18' and reference device settings 54 of the plurality of reference patients 42. Then, a cohort determination algorithm can be used to determine the cohort 44 for the patient 12. This cohort determination algorithm may be carried out in the cohort selection module 36.

One embodiment of how such a cohort determination algorithm may be implemented is explained below in detail. The following example is, however, not intended to limit the invention to the outlined concrete implementation. Rather, it is aimed at concretizing the invention with the help of one possible cohort determination scheme. According to the present invention, the choice of a statistically relevant cohort for one patient or for one device parameter may also be carried out in multiple other ways. According to one embodiment, the cohort determination may work as follows:

There is initially determined a statistical sample size. This statistical sample size denotes the number of reference patient 42 that have to be part of the cohort 44 in order to receive a statistically relevant result. In the following said statistical sample size is also being referred to as minimum statistically relevant cohort (MSRC). Then, the cohort 44 is assigned including the reference patients 42 with the closest profile data match. Then, the cohort size is modified to equal the determined MSRC. In a final step, the patient 12 under consideration is compared to the cohort 44.

For the following exemplary embodiment, it is assumed that the database 16 comprises reference profile data 18' of a plurality of reference patients 42 as well as their reference device settings 54. These reference patients 42 suffer from sleep apnea or obstructive sleep apnea. Then, e.g., the reference profile data 18' of the reference patients 42 include the personal profile parameters 20'-28': height, weight, neck size, typical level of alcohol or nicotine intake (may be recorded as actual units or perhaps on a scale such as 1-10) and the AHI. Further, the database 16 may include the following information for each personal profile parameter 20-28 provided by the patient 12 himself:

1. A value (i.e. an actual value for the profile parameter 20-28), either estimated or measured. As this value will later be extended into a range it can be considered the central value ("CV").
2. An importance factor ("IF") indicating the ability of that profile parameter 20-28 to influence the patient's 12 apnea condition. For instance this may be a factor on a scale of 1-10, with 1 being important and 10 meaning the profile parameter 20-28 that does not significantly influence the patient's apnea (or other health condition).
3. A range or range value for each profile parameter 20-28. This may be in the form of a percentage, for example +/−5%, incremental measurements, for example +/−5 cm, or increments in a range for example 2-3.
4. An upper limit ("UL") and a lower limit ("LL") for each profile parameter 20-28, which is calculated based on the range or range value.
5. A range factor ("RF") for each profile parameter 20-28 or, alternatively, a single RF for all profile parameters 20-28. The initial value of RF may be set to 0.1.

Thus, the database 16 then comprises for each profile parameter 20-28 of the patient 12 an IF, for each profile parameter 20-28 a CV (e.g. height CV=1.80 m), for each profile parameter 20-28 a range value (e.g. height range=0.1 m), for each profile parameter 20-28 both a UL and an LL (e.g. height LL=1.75 m, height UL=1.85 m) and an RF.

There is further added to the database 16 for each reference patient 42 a number of device parameters such as the flow rate, number of operating hours etc. For each device parameter the database 16 is able to store readings as per a given period (for example average reading over a night, a single reading taken each day etc.).

In the next step the MSRC is determined. This determination is usually based on the device parameters. The purpose of this step is to find the minimum number of reference patients 42 to which the patient 12 needs to be compared to give meaningful results (i.e. feedback information). If very fine granularity of results is required, the number of reference patients 42 in the comparison cohort 44 will need to be larger than if coarse granularity can be tolerated. For instance, if flow rate granularity of 0.1 l/m is required then more people in the comparison cohort 44 will be needed than if a granularity of 1 l/m is acceptable. One possibility for determining the MSRC is to use a predefined value defined by a physician or by a long-term statistical evaluation of patients such as, e.g. a pharmaceutical apparatus authorization study/report or the like. Alternatively, (standard) statistical sample size determination may be used. For example, if the parameter is flow rate measured in l/m, it needs to be decided whether an increment of 0.1 l/m or 1 l/m should be considered to be significant for distinguishing between differently chosen therapeutic device settings. This value is then used to calculate a confidence interval (e.g. 99%). Based upon this confidence interval the MSRC may be calculated. Thereby it may be possible to calculate a single MSRC for all therapeutic device settings or individually for the device setting under consideration. It may, however, also be possible to determine a separate cohort 44 for the device settings comprised in the suggested therapeutic device settings.

In the following it is outlined, how the cohort 44 may be determined based on one of profile parameter 20-28 (e.g. based on the above-mentioned example: height CV=1.80 m, height range=0.1 m, height LL=1.75 m and height UL=1.85 m, height RF=0.1):

1. Determine the number of reference patients 42, wherein each reference patient's profile parameter CV fits between the assessed LL and UL.
2. If the determined number of patients is lower than the MSRC, then the range value is increased (calculate a new upper range limit UL' and a new lower range limit LL') by considering both the IF and RF. This can be implemented according to:
   a. LL'=CV (range/2)*(1+(RF)*IF/10); and
   b. UL'=CV+(range/2)*(1+(RF)*IF/10).
   This process is repeated until the number of reference patients 42 within the limits is greater than the MSRC.
3. If the determined number of reference patients 42 is bigger than the MSRC, then the range value is decreased (calculate a new upper range limit, UL' and a new lower range limit LL') by considering both the IF and RF. This can be implemented according to:
   a. LL'=CV (range/2)*(1−(RF)*IF/10); and
   b. UL'=CV+(range/2)*(1−(RF)*IF/10).

This process is repeated until the number of reference patients 42 within the limits is smaller than the MSRC and then the last change is discarded to leave a number greater than the MSRC.

If there are further profile parameters, this algorithm may, for example, initially be carried out for the least important profile parameter (profile parameter to which the highest importance factor is assigned). For instance, it may be that the age of a person is more important than the height of a person when determining the flow rate of a medical ventilator. Then, the age can be assigned an importance factor of 2 and the height can be assigned an importance factor of 8. When determining the cohort 44 for the patient 12 as outlined above, it then makes sense to initially increase the range of the profile parameter height. It may thereby also be possible to further define a maximum possible range for each profile parameter defining the largest possible range.

As previously mentioned an individual cohort size (and an individual cohort) could be used for each device parameter of the therapeutic device settings or a single cohort size and cohort could be used for all device parameters.

In further embodiments of the present invention, it may also possible that, alternatively to mainly presenting how the reference patients 42 in the cohort 44 set their therapeutic devices, the feedback information already includes some sort of meta-information determined based thereupon. For instance, the feedback information may include a deviation parameter being indicative of the deviation of his/her chosen therapeutic device settings from the reference device settings of the reference patients 42 in the cohort.

Furthermore, both profile data (personal or reference profile data) and therapeutic device settings (as well as corresponding importance factors and range values) may also be contributed (partially) by a physician or medical support personal.

Still further, the database 16 may be based on appropriate data storage mediums, such as e.g. a hard disk drive, a flash drive, a flash memory or another type of data storage medium. The database 16 may also comprise the necessary control module or control processor in order to store and/or obtain information in/from the database. Further, the database 16 may be accessible and controllable by means of an appropriate database programming language such as, e.g. the Structured Query Language (SQL).

In yet another embodiment the interface 34 comprised in the patient feedback system 10 may be represented by a regular personal computer providing a keyboard and a screen that can be used by a patient, physician or other medical personnel to manually enter personal profile data and/or access the patient feedback system and the different modules thereof.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for treating a medical condition said system comprising:
    a therapeutic device;
    a data interface for receiving personal profile data of the patient, wherein the personal profile data includes a type of disease from which the patient suffers;
    a database for storing reference profile data and reference device settings from a plurality of reference patients using therapeutic devices, wherein the reference profile data for each reference patient includes the type of disease from which the reference patient suffers, and wherein the reference device settings include at least one device parameter being indicative of how a therapeutic device of a reference patient is configured;
    a cohort selection module that is part of the therapeutic device for comparing the personal profile data of the patient with the reference profile data of the reference patients in the database and for determining a cohort for the patient from the plurality of reference patients based upon said comparison, wherein said cohort comprises a subset of the reference patients having reference profile data similar to the personal profile data of the patient and using similar or the same therapeutic devices as the patient, wherein the reference profile data similar to the personal profile data of the patient includes the type of disease, and wherein determining the cohort further includes determining for one of the at least one device parameter a statistical sample size representing a minimum number of reference patients in the cohort depending on a required granularity of said device parameter to allow determining statistically relevant feedback information being related to said device parameter and being;
    a therapy module that is part of the therapeutic device for determining improved therapeutic device settings based on the reference device settings of the reference patients in the cohort; and
    a feedback unit that is part of the therapeutic device for determining feedback information for improving the use of the therapeutic device based on the reference device settings of the reference patients in the cohort and for providing said feedback information to the patient,
    wherein said feedback information includes the improved therapeutic device settings, and
    wherein said feedback information is directly fed into the therapeutic device by the feedback unit and responsive thereto the therapeutic setting of the therapeutic device is automatically adjusted to the improved therapeutic device settings.

2. The system according to claim 1, wherein the data interface is further configured to receive therapeutic device settings of the patient, and wherein the feedback information includes a deviation parameter being indicative of the deviations of the therapeutic device settings of the patient from the reference device settings of the reference patients in the cohort.

3. The system according to claim 1, further comprising a formatting module for converting the personal profile data received via the interface into a predefined format.

4. The system according to claim 1, wherein the personal profile data or the reference profile data, respectively, include at least one profile parameter being indicative of a sleep profile of the patient or a reference patient, respectively, in particular a sleep duration and/or an apnea-hypopnea index; physiological data of the patient or the reference patient, respectively, in particular the sex, age, weight or height of the patient or the reference patient, respectively; a vital sign of the patient or the reference patient, respectively; a medical history of the patient or the reference patient, respectively; and a type and/or a serial number of the therapeutic device used by the patient or the reference patient, respectively.

5. The system according to claim 4, wherein the personal profile data further include: an importance factor for the at least one profile parameter being indicative of the importance of said at least one profile parameter when determining the cohort; and a range value for the at least one profile parameter being indicative of a tolerable offset when determining the cohort.

6. The system according to claim 5, wherein the cohort selection module is configured to include the range value and the importance factor in the determination of the cohort for the patient.

7. The system according to claim 4, wherein the personal profile data further include a range value for the at least one profile parameter being indicative of a tolerable offset when determining the cohort; wherein said comparison of the personal profile data of the patient with the reference profile data of the reference patients is based on said range value for the at least one profile parameter; and wherein determining the cohort for the patient from the plurality of reference patients further includes adjusting said range value until a number of reference patients in the cohort is substantially equal to said statistical sample size.

8. The system according to claim 4, wherein receiving personal profile data of the patient includes receiving personal profile data from a monitoring device measuring the at least one profile parameter being indicative of the sleep profile and/or the vital sign of the patient.

9. The system according to claim 1, wherein the interface is further suitable for receiving personal profile data and/or therapeutic device settings from patients willing to contribute reference profile data or reference device settings to the database.

10. The system according to claim 1, wherein the therapeutic device is configured to provide a flow of pressurized gas to the patient.

11. A method for treating a medical condition a patient using a therapeutic device, said method comprising: receiving personal profile data of the patient, the personal profile data including a type of disease from which the patient suffers; storing reference profile data and reference device settings from a plurality of reference patients using therapeutic devices, the reference profile data for each reference patient including a type of disease from which the reference patient suffers, and wherein the reference device settings include at least one device parameter being indicative of how a therapeutic device of a reference patient is configured; comparing the personal profile data of the patient with the reference profile data of the reference patients in the database; determining a cohort for the patient from the plurality of reference patients based upon said comparison, wherein said cohort comprises a subset of the reference patients having reference profile data similar to the personal profile data of the patient and using similar or the same therapeutic devices as the patient, wherein the reference profile data similar to the personal prone data of the patient includes the type of disease, and wherein determining the cohort further includes determining for one of the at least one device parameter a statistical sample size representing a minimum number of reference patients in the cohort depending on a required granularity of said device parameter to allow determining statistically relevant feedback information being related to said device parameter; and determining improved device settings for improved use of the therapeutic device based on the reference device settings of the reference patients in the cohort; providing said improved device settings to the therapeutic device; and providing a treatment to the patient with the theraputic device being operated at the improved device settings.

12. Computer program comprising program code means for causing a computer to carry out the steps of the method as claimed in claim 11 when said computer program is carried out on the computer.

13. The system of claim 1, wherein the personal profile data includes both the type of disease and an extent to which the patient suffers therefrom, and wherein the reference profile data for each reference patient includes both the type of disease and an extent to which each reference patient suffers therefrom.

14. The system of claim 1, wherein the therapeutic device comprises a medical ventilator.

15. The method of claim 11, wherein the therapeutic device comprises a medical ventilator.

16. The system of claim 1, wherein the therapeutic device comprises a pressure-support system for treating the medical condition obstructive sleep apnea syndrome.

17. The method of claim 11, wherein the therapeutic device comprises a pressure-support system for treating the medical condition obstructive sleep apnea syndrome.

* * * * *